United States Patent [19]
Blitstein-Willinger et al.

[11] Patent Number: 5,466,713
[45] Date of Patent: Nov. 14, 1995

[54] ILOPROST WITH ACTION AGAINST CEREBRAL MALARIA

[75] Inventors: Eveline Blitstein-Willinger; Karin Sliwa-Hähnle, both of Berlin, Germany

[73] Assignee: Schering Aktiengesellschaft, Berlin, Germany

[21] Appl. No.: 104,068

[22] PCT Filed: Feb. 7, 1992

[86] PCT No.: PCT/DE92/00091

§ 371 Date: Dec. 3, 1993

§ 102(e) Date: Dec. 3, 1993

[30] Foreign Application Priority Data

Feb. 12, 1991 [DE] Germany .......................... 41 04 606.4

[51] Int. Cl.⁶ ...................... A61K 31/19; A61K 31/557
[52] U.S. Cl. ............................................................ 514/573
[58] Field of Search ............................................... 514/573

[56] References Cited

U.S. PATENT DOCUMENTS 4,497,830  2/1985  Skuballa et al. ..................... 514/573

OTHER PUBLICATIONS

Sliwa et al., "Prevention of Murine Cerebral Malaria by a Stable Prostacyclin Analog", *Infection And Immunity*, vol. 59, No. 10 (Oct. 1991), pp. 3846–3848.

*The Lancet*, vol. 84, Supplement 2 (Jul.–Dec. 1982), edited by M. J. Weston et al., "Prostacyclin in falciparim malaria", p. 609.

S. Palaoglu et al., "Cytoprotective effect of iloprost on isolated cortical brain tissue grafts in rats", *Chemical Abstracts*, Abstract No. 53008s, vol. 113, No. 7 (1990).

Borzeix et al., "Effects of new chemically and metabolically stable prostacyclin analogues (iloprost and ZK 96480) on early consequences of a transient cerebral oligemia, in the rat", *Prostaglandins*, vol. 35, No. 5 (May 1988), pp. 652–664.

*Primary Examiner*—J. D. Goldberg
*Attorney, Agent, or Firm*—Millen, White, Zelano & Branigan

[57] ABSTRACT

This invention relates to the use of iloprost for the production of an agent for treating cerebral malaria.

9 Claims, No Drawings

ILOPROST WITH ACTION AGAINST CEREBRAL MALARIA

This invention relates to an agent for treating cerebral malaria, which contains iloprost as active ingredient, as well as a process for the production of this agent.

Lancet, 1982, 609, already reported on the successful treatment of cerebral malaria, the most severe complication of Plasmodium falciparum malaria, with prostacyclin ($PGI_2$) on a single patient.

In addition, the WHO report "Severe and Complicated Malaria, Second Edition, Vol. 84, Suppl. 2, 1990, 1–65" mentions 2 additional unpublished cases, which were also treated with prostacyclin.

It has now been found that iloprost (I), its

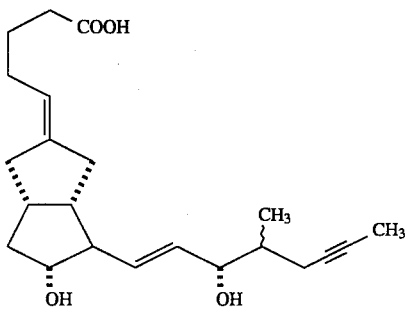

salts with physiologically compatible bases and its β-cyclodextrin clathrate are suitable in an advantageous way for treating cerebral malaria.

Although iloprost, in contrast to $PGI_2$ a stable prostacyclin derivative, has been known since 1980 by European patent application EP 11591, no other prostacyclin derivative has previously been tested in this indication. It is therefore reasonable to assume that a spontaneous healing is involved in the published case.

It has now been found, surprisingly, that iloprost is effective in the case of cerebral malaria.

For salt formation of iloprost, inorganic and organic bases are suitable, as they are known to one skilled in the art for the formation of physiologically compatible salts. For example, there can be mentioned: alkali hydroxides, such as sodium and potassium hydroxide, alkaline-earth hydroxides, such as calcium hydroxide, ammonia, amines, such as ethanolamine, diethanolamine, triethanolamine, N-methylglucamine, morpholine, tris-(hydroxymethyl)-methylamine, etc.

The β-cyclodextrin clathrate formation takes place according to EP 259468.

The production of iloprost is described in detail in EP 11591.

In EP 11591, the following pharmacological properties are described for the carbacyclin derivatives described there:

Lowering of the peripheral arterial and coronary vascular resistance, inhibition of the platelet aggregation and dissolution of platelet clots, myocardial cytoprotection; lowering of the systemic blood pressure without lowering stroke volume and coronary blood circulation at the same time; treatment of stroke, prophylaxis and therapy of coronary heart diseases, coronary thrombosis, of myocardial infarction, peripheral arterial diseases, arteriosclerosis and thrombosis, treatment of shock, inhibition of bronchoconstriction, inhibition of gastric acid secretion and cytoprotection of the gastric and intestinal mucous membrane; antiallergic properties, lowering of the pulmonary vascular resistance and the pulmonary blood pressure, stimulation of renal circulation, use instead of heparin or as adjuvant in dialysis or hemofiltration, preservation of dried blood plasma, especially of dried blood platelets, inhibition of labor pains, treatment of gestational toxemia, increase of cerebral blood circulation and antiproliferation.

The treatment of cerebral malaria by iloprost is not described and is also not directly connected with the other pharmacological properties described in EP 11591.

The dose of iloprost is 1–1500 μg/kg/day, if it is administered to human patients. The individual dose for the pharmaceutically acceptable vehicle is 0.01–100 mg.

The dosage of an i.v. administration as a continuous infusion in usual aqueous solvents, e.g., 0.9% NaCl solution, takes place preferably in dosages between 0.1 ng/kg/min and 0.1 μg/kg/min.

The invention thus relates also to pharmaceutical agents based on iloprost and usual adjuvants and vehicles.

The active ingredient according to the invention is to be used in connection with the auxiliary agents known and usual in galenicals, e.g., for the production of agents against cerebral malaria.

The invention also relates to a process for the production of the agent according to the invention, which is characterized in that in a way known in the art, the compound acting against cerebral malaria is put in a galenical formulation with the adjuvants and vehicles known in the art.

EXAMPLES

Mouse model for cerebral malaria

After inoculation with $1\times10^6$ parasitized erythrocytes (Plasmodium berghei ANKA) i.p. to 80–90% between the 7th and 14th days, CBA/CA mice develop the syndrome of cerebral malaria with neurological symptoms (slowing, paralysis, ataxia, convulsions), from which they die within a few hours (1–5 hours).

At that time, an only low-grade anemia with a parasitemia of only 8–10% is present. The surviving mice die after 3–4 weeks of severe anemia with a parasitemia of over 50%.

Grau et al. (Science, Vol. 237 (1987)) have been able to document the decisive role of TNF in the pathogenesis and prognosis of this disease by the following results:

a) At the time of the occurrence of cerebral complications, the mice susceptible to cerebral malaria show a clearly increased serum TNF level.

b) Passive immunization relative to mouse-TNF significantly reduces the occurrence of cerebral malaria in the case of CBA/CA mice infested with Plasmodium berghei.

c) The treatment with anti-TNF antibodies also prevents the histopathological changes, which are significant for cerebral malaria.

EXAMPLE 1

By intraperitoneal injection of 2% starch solution, a local sterile inflammation is placed in NMRI mice. After 3–5 days, the animals are killed and the macrophages extracted.

In vitro tests show that iloprost dose-dependently inhibits the TNF production of the NMRI-mice peritoneal macrophages induced by heat-labile antigen, which was extracted from Plasmodium berghei.

The nonadherent cells are separated.

To activate the macrophages, heat-stable soluble antigen, which is prepared with P. b. ANKA parasitized murine erythrocytes (2), is used.

As a TNF-assay, TNF-sensitive cell line WEHI 164 (commercially available) is used. The extent of the cell lysis of WEHI 164 is proportional to the amount of TNF present. In 96 cup flat-bottom microtiter plates, the culture supernatants and sera are titrated off in a dilution series. A titration series with TMU-TNF is used as a standard.

The number of surviving cells is determined based on the colorimetric MTT test.

The calculation is performed by the comparison with the standard titration series of TMU-TNF by probit analysis.

The test allows a determination of up to 0.5 U/ml of TNF. By adding an anti-TNF antiserum, a differentiation can be made between TNFα and TNFβ.

EXAMPLE 2

Use of iloprost in the animal model 15 mice are infested by the intraperitoneal administration of $1\times10^6$ parasitized erythrocytes. Simultaneously with the infestation, the administration of 1 µg of iloprost (100 µl s.c.) takes place in 6 mice. This treatment is continued daily at the same time until the 10th day.

The 9 mice of the control group are treated as described above, but receive 100 µl of NaCl instead of iloprost. The parasitemia is determined daily (blood smear, Giemsa stain).

Both groups achieve a 10% parasitemia on day 10 after the infestation.

Of the control group, 8 of the 9 mice with previous cerebral symptoms die between the 8th and 14th days. The mice of the iloprost group show no cerebral symptoms at this time.

The last mouse of the control group as well as the mice of the iloprost group die as a result of severe anemia between the 24th and 30th days after the infestation.

EXAMPLE 3

The serum TNF levels of the untreated and the iloprost-treated mice are tested.

Iloprost still significantly inhibits the TNF levels in the serum even 4 days after the last injection.

BIBLIOGRAPHY

1. G. Grau, L. Fajardo, P. Piguet, B. Allet, P. Lambert, P. Vassalli, Science, Vol. 237 (1987)
2. J. Taverne, C. Bate, Parasite Immunology 1990, 12, 33–43

We claim:

1. A method of treating cerebral malaria, comprising administering to a patient in need thereof a composition comprising an effective amount of iloprost or a physiological salt thereof.
2. A method according to claim 1, wherein the composition further comprises β-cyclodextrin.
3. A method according to claim 1, wherein the amount of iloprost is about 1 to about 1500 µg/kg/day.
4. A method according to claim 1, wherein the composition is administered intravenously.
5. A method according to claim 4, wherein the iloprost is administered in an amount of from about 0.1 ng/kg/min. to about 0.1 µg/kg/min.
6. A method according to claim 1, wherein the composition further comprises an adjuvant.
7. A method according to claim 1, wherein the concentration of TNF in said patient is reduced or inhibited.
8. A method according to claim 1, wherein the cerebral malaria results from *Plasmodium* infection.
9. A method according to claim 1, wherein the cerebral malaria results from *Plasmodium falciparum* infection.

* * * * *